United States Patent
Sas et al.

(10) Patent No.: US 7,125,853 B2
(45) Date of Patent: *Oct. 24, 2006

(54) **BICYCLIC CARBOHYDRATE COMPOUNDS USEFUL IN THE TREATMENT OF INFECTIONS CAUSED BY *FLAVIVIRIDAE* SP., SUCH AS HEPATITIS C AND BOVINE VIRAL DIARRHEA VIRUSES**

(75) Inventors: Benedikt Sas, Stekene (BE); Johan Van hemel, Antwerpen (BE); Jan Vandenkerckhove, Zichem (BE); Eric Peys, Balen (BE); Johan Van der Eycken, Ninove (BE); Bart Ruttens, Ghent (BE); Jan Balzarini, Heverlee (BE); Eric De Clercq, Bierbeek (BE); Johan Neyts, Kessel Lo (BE)

(73) Assignee: Kemin Pharma B.V.B.A., Des Moines, IA (US)

( * ) Notice: Subject to any disclaimer, the term of this patent is extended or adjusted under 35 U.S.C. 154(b) by 346 days.

This patent is subject to a terminal disclaimer.

(21) Appl. No.: 10/743,111

(22) Filed: Dec. 22, 2003

(65) Prior Publication Data

US 2004/0209823 A1    Oct. 21, 2004

Related U.S. Application Data

(60) Provisional application No. 60/438,475, filed on Jan. 7, 2003.

(51) Int. Cl.
- A01N 43/04 (2006.01)
- A01N 43/16 (2006.01)
- A61K 31/70 (2006.01)
- A61K 31/35 (2006.01)

(52) U.S. Cl. .......... 514/23; 514/25; 514/451; 549/364; 549/365

(58) Field of Classification Search ......... 514/23, 514/25, 451; 549/364, 365
See application file for complete search history.

(56) References Cited

U.S. PATENT DOCUMENTS

| 6,034,073 | A  * | 3/2000 | Wright ............ 514/77 |
| 6,518,253 | B1 * | 2/2003 | Tam ............... 514/42 |
| 2003/0158243 | A1 * | 8/2003 | Sas et al. ........ 514/375 |
| 2003/0199521 | A1 * | 10/2003 | Dykstra et al. ... 514/256 |
| 2004/0180838 | A1 * | 9/2004 | Sas et al. ........ 514/23 |
| 2005/0059612 | A1 * | 3/2005 | Sas et al. ........ 514/23 |
| 2005/0267048 | A9 * | 12/2005 | Sas et al. ........ 514/25 |

FOREIGN PATENT DOCUMENTS

| WO | WO 03/082846 A1 | 10/2003 |
| WO | WO 04/014929 A1 | 2/2004 |

OTHER PUBLICATIONS

Database CAPLUS on STN, AN 2001:544756. Espinola et al. "Synthetic Flux-Promoting Polyether Modstl: Cation Flux Dependence on Polyoxyethylene Chain Length", Isreal Journal of Chemistry, 2000, vol. 40, Issue 3-4.

* cited by examiner

Primary Examiner—Shaojia Anna Jiang
Assistant Examiner—Traviss C. McIntosh, III
(74) Attorney, Agent, or Firm—Kent A. Herink; Daniel A. Rosenberg; Emily E. Harris

(57) ABSTRACT

We describe the use of bicyclic carbohydrates for the treatment of hepatitis C virus infections. Different bicyclic carbohydrates were tested in vitro against DNA-viruses, retro-viruses and *Flaviviridae* sp., an important family of human and animal RNA pathogens. Significant activity was observed against the bovine viral diarrhea virus (BVDV). As pestiviruses, such as BVDV, share many similarities with hepatitis C virus (HCV), the bicyclic carbohydrates in general and the preferred bicyclic carbohydrates more specifically are expected to be a treatment for hepatitis C viral infections.

5 Claims, 3 Drawing Sheets

BICYCLIC CARBOHYDRATE COMPOUNDS USEFUL IN THE TREATMENT OF INFECTIONS CAUSED BY *FLAVIVIRIDAE* SP., SUCH AS HEPATITIS C AND BOVINE VIRAL DIARRHEA VIRUSES

This application claims priority to U.S. Patent Application Ser. No. 60/438,475, filed Jan. 7, 2003.

BACKGROUND OF THE INVENTION

The invention relates generally to bicyclic carbohydrate compounds useful in the treatment of infections caused by *Flaviviridae sp.* and, more specifically, to such compounds useful in the treatment or amelioration of infections caused by hepatitis C, bovine viral diarrhea, classical swine fever, West Nile and dengue viruses.

Hepatitis C was first recognized as a separate disease entity in 1975 when the majority of cases of transfusion-associated hepatitis were found not to be caused by the only two hepatitis viruses recognized at the time, hepatitis A virus and hepatitis B virus. The disease was called "non-A non-B hepatitis," and it was demonstrated to be transmissible to chimpanzees. It was not until 1989, however, that the cloning and sequencing of the viral genome of the non-A non-B hepatitis virus was first reported and the virus was renamed "hepatitis C virus" (HCV). Tests for antibody to HCV quickly followed, and screening for such antibody remains a principal method of diagnosis.

Hepatitis C virus shares virological and genetic characteristics with the *Flaviviridae*. Its genomic organization is similar to that of the flaviviruses and pestiviruses and shares slight sequence identity with these viruses, especially the pestiviruses. Each of these groups of viruses comprises a separate genus within the *Flaviviridae*: flavivirus, pestivirus and hepacivirus. Hepatitis C virus is a spherical enveloped virus of approximately 50 nm in diameter. The genome of HCV is a single-strand linear RNA of positive sense. It is unsegrnented. A 5' non-coding (NC) region consists of approximately 340 nucleotides. Immediately downstream is a single large open reading frame (ORF) of approximately 9000 nucleotides. Finally there is a 3' NC region that consists of approximately 100 nucleotides. The genome of HCV is highly heterogeneous. The most highly conserved regions of the genome are parts of the 5' NC region and the terminal 3' NC region. The most highly conserved region of the ORF is the capsid gene. In contrast, the most heterogeneous portions of the genome are the genes encoding the envelope proteins. Based on their genetic heterogeneity, HCV strains can be divided into major groups, called types or genotypes (and provisionally classified as separate species) of the virus. Within types, HCV isolates have been grouped into numerous subtypes. Finally, individual isolates consist of heterogeneous populations of the viral genomes that comprise "quasispecies" or "swarms" of closely related but different viruses. Some genotypes of HCV appear to be geographically restricted; others have worldwide distribution. More extensive genetic analysis of HCV has revealed that the hierarchical classification of isolates into types, subtypes, and isolates is somewhat artifactual and the viruses probably exist as a continuum of genetic diversity. The consequence of the genetic diversity of HCV is a virus that has the ability to escape the immune surveillance of its host, leading to a high rate (more than 80 percent) of chronic infections and lack of immunity to re-infection in repeatedly exposed individuals. Both chronicity and lack of solid immunity probably result from the emergence of minor populations of the virus quasispecies that vary in sequence (www.HEPNET.com, the Hepatitis Information Network; Challand R., Young R. J. (1997) Antiviral Chemotherapy. Biochemical & Medicinal Chemistry Series. Spektrum Academic Publishers, Oxford, pp. 87–92; Cann A. J. (1997) Principles of Molecular Virology. Second Edition. Academic Press, San Diego, pp. 230–235). Other important *Flaviviridae* that give rise to medical unmet needs are West Nile virus and the virus causing dengue.

Therefore, a strong medical need exists to discover and develop new bioactive molecules that can be used to treat *Flaviviridae* infections with fewer or reduced side effects and better efficiency compared to the current available treatments.

SUMMARY OF THE INVENTION

It has been discovered that certain bicyclic carbohydrates having the generic formula:

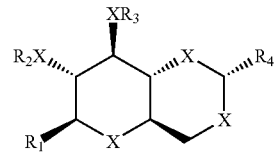

wherein $R_1$ is aryl or benzyl, $R_2$ and $R_3$ are either alkyl or aryl, $R_4$ is aryl and X is either O, N or S, have activity against infections caused by *Flaviviridae*, including hepatitis C, bovine viral diarrhea, classical swine fever, West Nile and dengue viruses. Representative, presently preferred bicyclic carbohydrates are described in this application, although it will be apparent to those skilled in the art that other bicyclic carbohydrates compounds will be useful in the treatment of infections caused by *Flaviviridae*. Also included are pharmaceutically acceptable salts of these compounds.

DETAILED DESCRIPTION OF PREFERRED EMBODIMENTS

Figure 1:
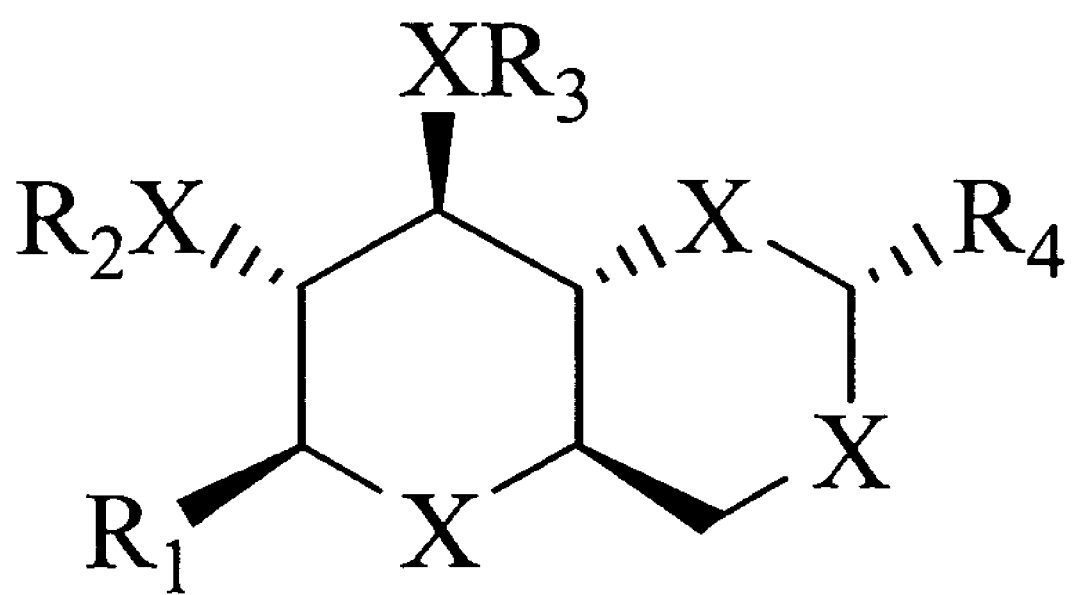
FIG. 1 is a chemical structure of the bicyclic carbohydrates of the present invention and designated Formula A.

The *Flaviviridae* is an important family of human and animal RNA viral pathogens (Rice CM. 1996. *Flaviviridae: the viruses and their replication*. In: Fields BN, Knipe DM, Howley PM, eds. Fields virology. Philadelphia: Lippincott-Raven Publishers. Pp 931–960). The three currently recognised genera of the *Flaviviridae* exhibit distinct differences in transmission, host range and pathogenesis. Members of this classical flavivirus are the yellow fever virus, dengue virus and the pestiviruses, such as bovine viral diarrhea virus (BVDV) and the classical swine fever virus (CSFV). The most recently characterized member of this family is the common and exclusively human pathogen, hepatitis C virus (HCV). *Flaviviridae* are single strand RNA viruses having (+) sense RNA genome polarity. Other virus families with (+) sense RNA include the *Picornaviridae, Togaviridae, Caliciviridae* and the *Coronaviridae*.

The inventive compounds may be used in their native form or as salts. In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, acetate, ascorbate, benzoate, citrate, etoglutarate, glycerophosphate, malonate, methanesulfonate, succinate, and tartarate. Suitable inorganic salts may also be formed, including bicarbonate, carbonate, hydrochloride, nitrate, and sulfate, salts.

Compounds of the present invention can conveniently be administered in a pharmaceutical composition containing the compound in combination with a suitable excipient, the composition being useful in combating viral infections. Depending on whether the preparation is used to treat internal or external viral infections, the compounds and compositions of the present invention can be administered parenterally, topically, intravaginally, orally, or rectally.

For parenteral administration, solutions of the active compound or its salts can be prepared in water, optionally mixed with a nontoxic surfactant. Dispersions can also be prepared in glycerol, liquid polyethylene glycols, triacetin, and mixtures thereof and in oils.

Useful dosages of the compound can be determined by comparing their in vitro activity. Methods for the extrapolation of effective dosages to humans are known to the art.

The compound is conveniently administered in unit dosage form; for example, containing 0.1 to 2000 mg, conveniently 100 to 1000 mg, most conveniently, 100 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 1 to 30 mg/kg, preferably 1 to 10 mg/kg of mammal body weight.

The exact regimen for administration of the compound and compositions disclosed herein will necessarily be dependent upon the needs of the individual subject being treated, the type of treatment and, of course, the judgment of the attending practitioner. The compounds of the present invention can be administered to an animal in need of treatment. In most instances, this will be a human being, but the treatment of livestock and companion animals is also specifically contemplated as falling within the scope of the instant invention.

Methods and Materials

Synthesis of the Compounds of Formula A

The compounds were synthesized as follows:

1. Synthesis of Compound A1 and Compound A2

Figure 2:
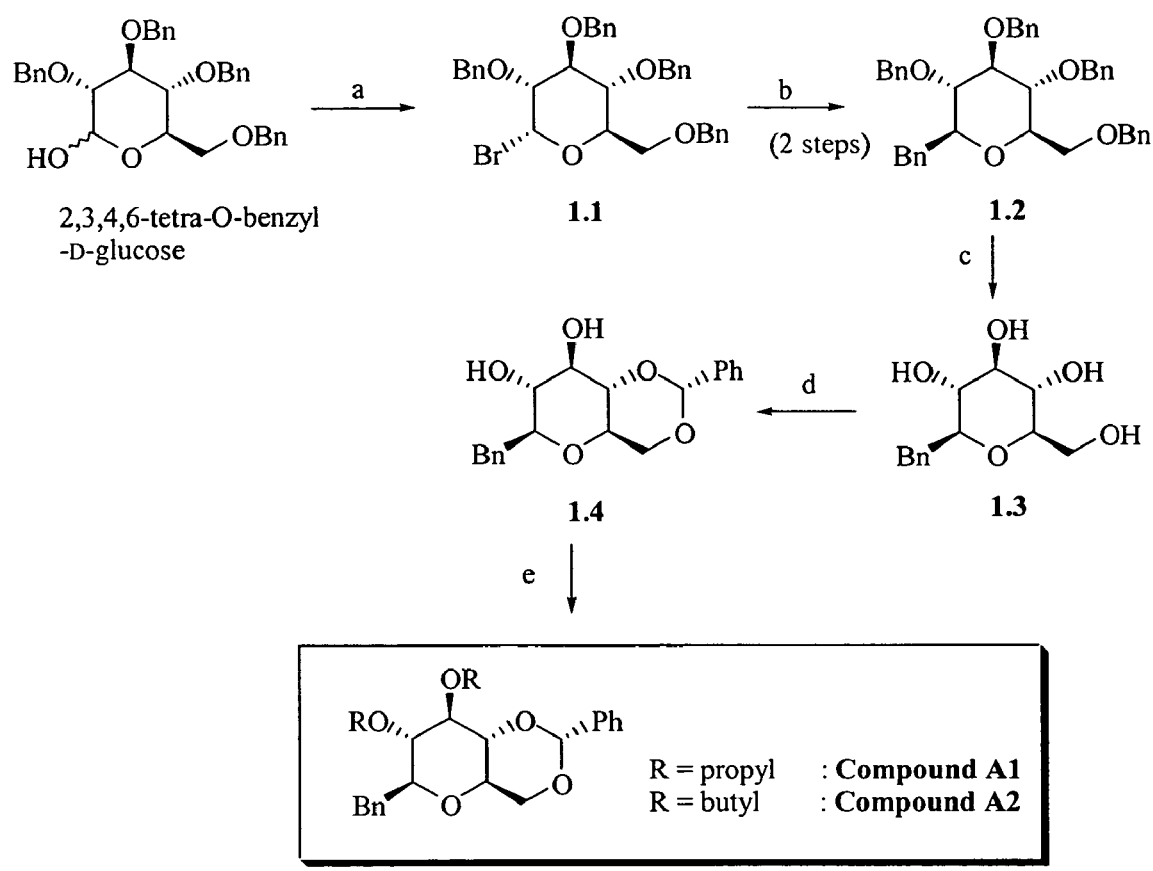
FIG. 2 is a diagrammatic representation of the scheme of synthesis of Compound A1 and Compound A2.

The synthesis of Compound A1 and Compound A2 is illustrated in FIG. 2.

Synthesis of Compound 1.1

To a solution of 2,3,4,6-tetra-O-benzyl-D-glucose (10.0 g, 18.5 mmol) in $CH_2Cl_2$ (125 ml) and DMF (6.25 ml) are added drop-wise at RT (room temperature) to a solution of oxalylbromide (2.5 ml of a 10 M solution in $CH_2Cl_2$, 1.35 eq). This is accompanied by a vigorous gas formation. The reaction mixture is stirred for 60 min at RT under Ar-atmosphere. The reaction mixture is then poured in ice water (125 ml). After separation of the phases, the organic layer is washed with ice water (2×125 ml). After drying over $MgSO_4$, filtration and evaporation in vacuo, Compound 1.1 (FIG. 1) is obtained as a yellow oil which is used in the next reaction step without further purification.

Formula: $C_{34}H_{35}BrO_5$ Molecular weight: 603.55 $R_f$: 0.53 (cyclohexane/ethyl acetate 85:15) $^1$H-NMR (500 MHz, $CDCl_3$): [δ (ppm); J (Hz)] 7.37 (3H, m), 7.33 (5H, m), 7.31 (5H, m), 7.28 (5H, m), 7.15 (2H, m), 6.43 (1H, d, J=3.7), 4.98 (1H, d, J=5.0), 4.83 (2H, dd,app. t, j=10.9), 4.58 (1H, d, J=12.1), 4.50 (1H, d, J=10.7), 4.46 (2H, d, J=12.1), 4.06 (1H, m), 4.03 (1H, dd, app. t, J=9.2), 3.80 (1H, m), 3.78 (1H, m), 3.76 (1H, d, J=4.6), 3.65 (1H, dd, J=11.0, 2.0), 3.54 (1H, dd, J=9.2, 3.7)

Synthesis of Compound 1.2

To a solution of Compound 1.1 (18.5 mmol theoretically) in dry $Et_2O$ (250 ml), cooled to 0° C., benzylmagnesium chloride (150 ml of a 1 M-opl. in $Et_2O$, 8 eq) is added slowly. The mixture is stirred at 0° C. for 1 hour, then the temperature is brought to room temperature slowly. After stirring overnight at room temperature, the reaction mixture is poured in $H_2O$ (500 ml) and AcOH, after which the phases are separated. The organic phase is then washed with 3×500 ml saturated $NaHCO_3$-sol. and 250 ml saturated NaCl-sol. Drying over $MgSO_4$, filtration and evaporation in vacuo, yields the crude product. This is purified by column chromatography (60–230 mesh silica, gradient: toluene:cyclohexane 8:2, toluene, cyclohexane:ethyl acetate 9:1), yielding 6.47 g of Compound 1.2 (57% over 2 steps) as a colorless oil.

Formula: $C_{41}H_{42}O_5$ Molecular weight: 614.78 $R_f$: 0.15 (cyclohexane/diethylether 9:1) $[α]_D^{20}$=+85.3°; $[α]_{365}^{20}$=+88.1°(c=0.60 in chloroform) IR(KBr): $(cm^{-1})$2862, 2360, 1604, 1496, 1454, 1360, 1209, 1085, 1028, 735, 697, 668 ES-MS: 632=$[M+NH_4]^{+1}$H-NMR (500 MHz, $CDCl_3$): [δ (ppm); J (Hz)] 7.36 (5H, m), 7.34 (5H, m), 7.31 (5H, m), 7.29 (5H, m), 7.26 (2H, m), 7.22 (3H, m), 4.96 (1H, d, J=11.0), 4.95 (1H, d, J=11.0), 4.91 (1H, d, J=11.0), 4.84 (1H, d, J=10.8), 4.69 (1H, d, J=11.0), 4.62 (1H, d, J=10.8), 4.59 (1H, d, J=12.2), 4.52 (1H, d, J=12.2), 3.74 (1H, dd, app. t, J=9.0), 3.69 (1H, m), 3.68 (1H, m), 3.66 (1H, dd, app. t, J=9.3), 3.52 (1H, ddd, J=18.3, 9.2, 2.3), 3.37 (1H, dd, app. t, J=9.0), 3.36 (1H, m), 3.17 (1H, dd, J=14.3, 2.0), 2.75 (1H, dd, J=14.3, 8.8) APT-NMR (125 MHz, $CDCl_3$): δ (Ppm) 138.9 (C), 138.7 (C), 138.5 (C), 138.3 (C), 138.2 (C), 129.7 (CH), 128.6 (CH), 128.6 (CH), 128.5 (CH), 128.4 (CH), 128.2 (CH), 128.0 (CH), 127.9 (CH), 127.8 (CH), 127.7 (CH), 127.6 (CH), 126.2 (CH), 87.5 (CH), 81.8 (CH), 80.1 (CH), 79.0 (CH), 78.7 (CH), 75.7 ($CH_2$), 75.2 ($CH_2$), 75.1 ($CH_2$), 73.5 ($CH_2$), 69.0 ($CH_2$), 38.0 ($CH_2$)

Synthesis of Compound 1.3

To a solution of Compound 1.2 (6.0 g, 9.76 mmol) in absolute EtOH (240 ml), Pd/C (600 mg, 10 mol %) is added at room temperature. The reaction mixture is shaken for 5 hours in a Parr apparatus under 4 atm $H_2$-gas. Filtration over celite and concentration in vacuo yields 2.62 g residue as a white-yellow foam. Purification hereof by column chromatography (60–230 mesh, $CH_2Cl_2$:MeOH 9:1) yields 2.46 g of Compound 1.3 as a white foam (99%)

Formula: $C_{13}H_{18}O_5$ Molecular weight: 254.28 $R_f$: 0.14 (dichloromethane/methanol 9:1) IR(KBr): $(cm^{-1})$ 3381, 2922, 2360, 2341, 1641, 1603, 1496, 1454, 1379, 1308, 1226, 1079, 1031, 897, 754, 701, 668 ES-MS: 272=[254+

NH$_4$]$^{+1}$H-NMR (500 MHz, CDCl$_3$): [δ (ppm); J (Hz)] 7.29 (2H, d, J=7.0), 7.22 (2H, dd, app. t, j=7.3), 7.14 (1H, m), 3.75 (1H, dd, J=11.9, 2.4), 3.60 (1H, dd, J=11.8, 5.4), 3.35 (1H, m), 3.32 (1H, m), 3.25 (1H, dd, app. t, J=9.4), 3.15 (1H, m), 3.12 (1H, m), 3.09 (1H, dd, app. t, J=9.3), 2.69 (1H, dd, J=14.5, 8.5) APT-NMR (125 MHz, CD$_3$OD): δ (ppm) 139.1 (C), 129.4 (CH), 127.6 (CH), 125.6 (CH), 80.4 (CH), 80.1 (CH), 78.6 (CH), 73.7 (CH), 70.6 (CH), 61.6 (CH$_2$), 37.4 (CH$_2$)

Synthesis of Compound 1.4

To a solution of Compound 1.3 (1.0 g, 3.93 mmol) in dimethylformamide (38.6 ml), benzaldehyde dimethyl acetal (708 µl, 1.2 eq) and D(+)-10-camphorsulfonic acid (274 mg, 0.3 eq) are added successively at room temperature. The reaction mixture is stirred for 2 h at room temperature under Ar-atmosphere. The work-up starts by diluting with EtOAc (150 ml). Then the solution is washed with 1N NaOH-sol. (2×150 ml), sat. NaHCO$_3$-sol. (2×100 ml) and sat. NaCl-sol. (2×100 ml). Drying over MgSO$_4$, filtration and concentration in vacuo yields 1.52 g white solid residue. Purification by column chromatography (60–230 mesh silica, CH$_2$Cl$_2$:MeOH 99:1) yields 940 mg of Compound 1.4 (70%) as a white solid.

Formula: C$_{20}$H$_{22}$O$_5$ Molecular weight: 342.39 R$_f$: 0.20 (cyclohexane:ethyl acetate 6:4) Melting point: 43–44° C. [α]$_D^{20}$=−6.9°; [α]$_{365}^{20}$=−10.7 (c=0.60 in chloroform) IR(KBr): (cm$^{-1}$)3478, 3031, 2871, 2360, 1604, 1497, 1454, 1385, 1317, 1299, 1271, 1212, 1124, 1099, 1077, 998, 973, 919, 673, 699, 668, 655, 625, 552, 510 ES-MS: 343=[M+H]$^{+1}$H-NMR (500 MHz, CDCl$_3$): [δ (ppm); J (Hz)] 7.49 (2H, m), 7.38 (3H, m), 7.31 (2H, m), 7.28 (2H, m), 7.25 (1H, m), 5.51 (1H, s), 4.28 (1H, dd, J=10.5, 4.8), 3.74 (1H, dd, app. t, J=8.7), 3.68 (1H, dd, app. t, J=10.0), 3.58 (1H, ddd, J=9.6, 8.2, 2.6), 3.43 (1H, dd, app. t, J=9.2), 3.39 (1H, m), 3.38 (1H, dd, J=10.5, 4.0), 3.18 (1H, dd, J=14.4, 2.5), 2.93 (1H, br s), 2.79 (1H, dd, J=14.4, 7.9), 2.69 (1H, br s) APT-NMR (125 MHz, CDCl$_3$): δ (Ppm) 138.0 (C), 137.1 (C), 129.8 (CH), 129.4 (CH), 128.4 (CH), 128.2 (CH), 126.4 (CH), 126.3 (CH), 101.9 (CH), 81.1 (CH), 80.3 (CH), 75.5 (CH), 73.8 (CH), 70.1 (CH), 68.9 (CH$_2$), 37.9 (CH$_2$)

Synthesis of Compound A1

To a solution of Compound 1.4 (100 mg, 0.292 mmol), cooled to 0° C., NaH (51 mg 60% dispense, 4 eq) is added. The mixture is then stirred for 30 min at 0° C. under Ar-atmosphere. Then n-propylbromide (133 µl, 5 eq) is slowly added dropwise. After 10 min at 0° C., stirring is continued overnight at room temperature. After TLC-analysis additional 2 eq NaH and 1 eq n-PrBr are added. After stirring for 4 h at room temperature, the reaction mixture is poured in H$_2$O (25 ml), followed by extraction with 3×30 ml Et$_2$O. The combined organic layers are washed with 50 ml sat. NaCl-sol. and dried over MgSO$_4$. Filtration and concentration in vacuo yields 144 mg white crystalline residue. After purification by column chromatography (230–400 mesh silica, pentane:ether 9:1), Compound A1 is obtained as a white crystalline product (117 mg, 94%).

Formula: C$_{26}$H$_{34}$O$_5$ Molecular weight: 426.55 R$_f$: 0.25 (pentane:ether 9:1) Melting point: 76–77° C. [α]$_D^{20}$=−41.4°; [α]$_{365}^{20}$=−127.6° (c=1.02 in chloroform) IR (KBr): (cm$^{-1}$) 2963 (m), 2918 (m), 2873 (m), 1454 (m), 1369 (m), 1121 (s), 1104 (s) 1089 (s), 1030 (m), 1008 (m), 968 (m), 951 (m), 748 (s), 697 (s), 652 (m) EI-MS: (m/z) 43 (86), 91 (100), 115 (39), 149 (26), 176 (17), 217 (5), 251 (3), 277 (32), 208 (1), 335 (3), 366 (2), 426 (8) [M$^+$], 427 (2) [M$^+$+1]

$^1$H-NMR (500 MHz, CDCl$_3$): [δ (ppm); J (Hz)] 7.48–7.46 (2H, m), 7.38–7.33 (3H, m), 7.30–7.20 (5H, m), 5.52 (1H, s), 4.24 (1H, dd, J=10.4, 5.0), 3.92 (1H, dt, J=8.8, 6.6), 3.86 (1H, dt, J=9.3, 6.6), 3.65 (1H, dd, app t, J=10.4), 3.64 (1H, dt, J=9.3, 6.8), 3.57–3.48 (4H, m), 3.29 (1H, ddd, app dt, J=10.0, 5.0), 3.15 (1H, dd, J=14.3, 2.0), 3.08 (1H, dd, J=9.3, 8.3), 2.70 (1H, dd, J=14.3, 8.7), 1.62 (4H, m), 0.98 (3H, t, J=7.4), 0.93 (3H, t, J=7.4) APT-NMR (125 MHz, CDCl$_3$): δ (ppm) 139.5 (C), 138.5 (C), 130.5 (CH), 129.7 (CH), 129.1 (CH), 129.0 (CH), 127.1 (CH), 126.9 (CH), 101.8 (CH), 84.4 (CH), 83.2 (CH), 82.6 (CH), 81.6 (CH), 76.1 (CH$_2$), 75.7 (CH$_2$), 71.1 (CH), 69.8 (CH$_2$), 39.1 (CH$_2$), 24.5 (CH$_2$), 24.5 (CH$_2$), 11.6 (CH$_3$), 11.6 (CH$_3$)

Synthesis of Compound A2

To a solution of Compound 1.4 (100 mg, 0.292 mmol), cooled to 0° C., NaH (51 mg 60% dispense, 4 eq.) is added. The mixture is stirred at 0° C. under Ar-atmosphere for 30 min. Then n-butylbromide (157 µl, 5 eq) is slowly added drop-wise. After stirring for 10 min at 0° C., stirring is continued overnight at room temperature. After TLC-analysis additional 2 eq NaH and 1 eq n-BuBr are added. After 5 h stirring at room temperature, the reaction mixture is poured in H$_2$O (25 ml), and the solution is extracted with met 3×30 ml Et$_2$O. The combined organic phases are washed with 50 ml sat. NaCl-sol. and dried over MgSO$_4$. Filtration and concentration in vacuo yield 168 mg white-yellow residue. Purification by column chromatography (230–400 mesh silica, pentane:ether 92:8) yields 125 mg white crystalline Compound A2 (94%).

Formula: C$_{28}$H$_{38}$O$_5$ Molecular weight: 454.60 R$_f$: 0.24 (pentane:ether 92:8) Melting: 69–70° C. [α]$_D^{20}$=−38.7°; [α]$_{365}^{20}$=−120.8° (c=0.98 in chloroform) IR (KBr): (cm$^{-1}$) 2963 (s), 2929 (s), 2873 (s), 1454 (m), 1375 (m), 1172 (m), 1092 (s), 1030 (m), 1008 (m), 968 (m), 748 (m), 697 (s) EI-MS: (m/z) 57 (75), 91 (100), 129 (49), 177 (12), 189 (19), 235 (2), 291 (36), 307 (4), 363 (2), 454 (5) [M$^+$]$^1$H-NMR (500 MHz, CDCl$_3$): [δ (ppm); J (Hz)] 7.49–7.47 (2H, m), 7.38–7.34 (3H, m), 7.31–7.21 (5H, m), 5.52 (1H, s), 4.24 (1H, dd, J=10.4, 5.0), 3.96 (1H, dt, J=8.9, 6.6), 3.90 (1H, dt, J=9.4, 6.6), 3.71–3.64 (2H, m), 3.59 (1H, dt, J=8.9, 6.6), 3.55–3.48 (3H, m), 3.29 (1H, ddd, app dt, J=9.5, 5.0), 3.15 (1H, dd, J=14.3, 1.9), 3.08 (1H, dd, app t, J=8.8), 2.97 (1H, dd, J=14.3, 8.7), 1.65–1.55 (4H, m), 1.49–1.35 (4H, m), 0.96 (3H, t, J=7.4), 0.90 (3H, t, j=7.4) APT-NMR (125 MHz, CDCl$_3$): δ (ppm) 140.0 (C), 139.0 (C), 131.0 (CH), 130.2 (CH), 129.6 (CH), 129.5 (CH), 127.6 (CH), 127.4 (CH), 102.4 (CH), 84.9 (CH), 83.7 (CH), 83.1 (CH), 82.1 (CH), 74.7 (CH$_2$), 74.3 (CH$_2$), 70.4 (CH), 64.5 (CH$_2$), 39.6 (CH$_2$), 34.0 (CH$_2$), 33.9 (CH$_2$), 20.8 (CH$_2$), 20.7 (CH$_2$), 15.4 (CH$_3$), 15.3 (CH$_3$)

2. Synthesis of Compound A3

Figure 3:
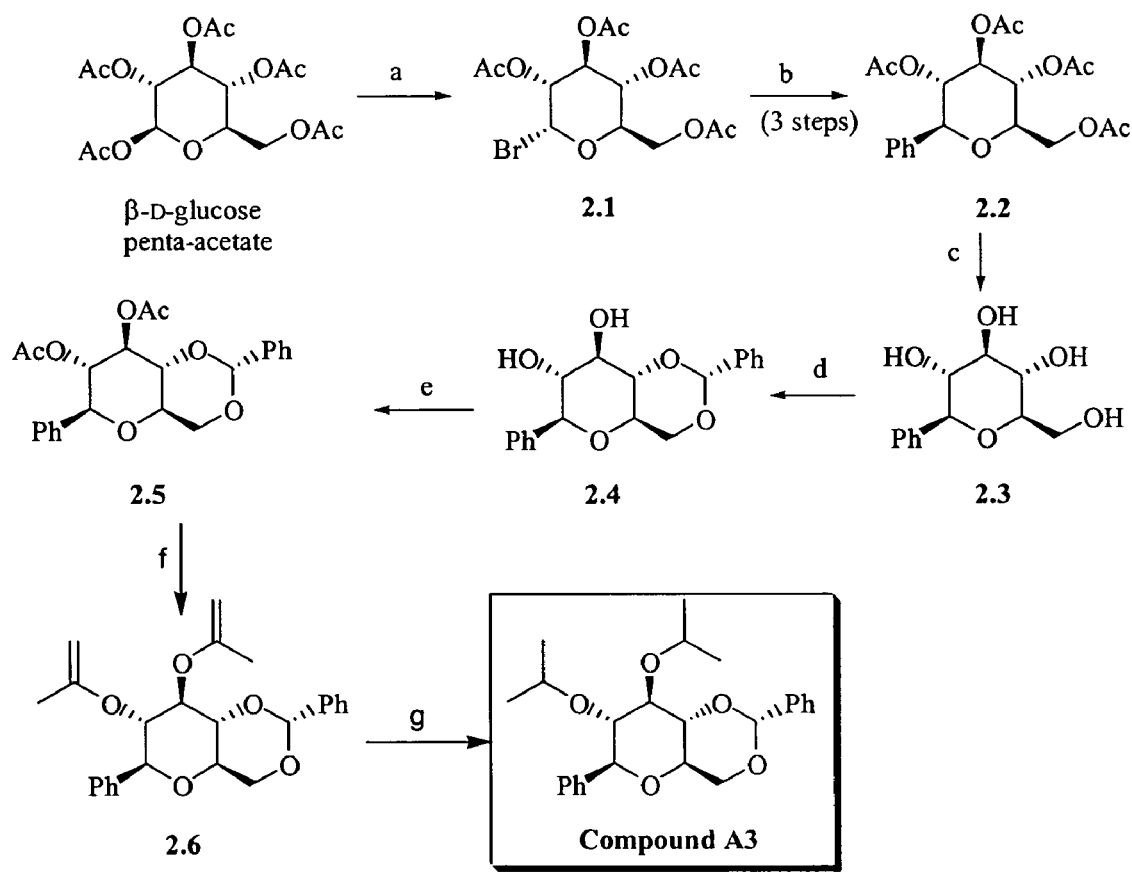
FIG. 3 is a diagrammatic representation of the scheme of synthesis of Compound A3.

The synthesis of Compound A3 is illustrated in FIG. 3.

Synthesis of Compound 2.1

To (β)-D-glucose penta-acetate (24.6 g, 63.0 mmol) was added a solution of hydrogen bromide in acetic acid (33 wt %, 100 ml). A dark brown color immediately appears. The reaction mixture was stirred at room temperature for 30 minutes under argon atmosphere. Subsequently the solvent was removed by azeotropic distillation in vacuo with toluene (4×50 ml), yielding a green-brown solid Compound 2.1. The crude product was used in the next reaction step without further purification.

Formula: C$_{14}$H$_{19}$O$_9$Br Molecular weight: 411.20 R$_f$: 0.46 (cyclohexane/ethyl acetate 1:1) IR(KBr): 2962, 2360, 2342, 1748, 1435, 1369, 1218, 1162, 1112, 1079, 1042, 911, 752, 668, 601, 563 cm$^{-1}$ ES-MS: 433=[410+Na]$^+$, 435=[412+Na$^+$]$^1$H-NMR (500 MHz, CDCl$_3$): [δ (ppm); J (Hz)] 6.61

(1H, d, J=4.0), 5.56 (1H, dd, app. t, j=9.7), 5.16 (1H, dd, app. t, J=9.7), 4.84 (1H, dd, J=10.0, 4.0), 4.33 (1H, m), 4.30 (1H, m), 4.13 (1H, dd, J=12.3, 1.5), 2.11 (3H, s), 2.10 (3H, s), 2.05 (3H, s), 2.03 (3H, s) $^{13}$C-NMR (125 MHz, CDCl$_3$): δ (ppm) 170.37, 169.70, 169.64, 169.31, 86.34, 71.91, 70.39, 69.94, 66.94, 60.76, 20.48, 20.48, 20.38, 20.38

Synthesis of Compound 2.2

To a solution of phenylmagnesium bromide (200 ml of a 3M solution in diethyl ether, 600 mmol, 9.5 eq) in dry diethyl ether (500 ml), cooled to 0° C., was added a solution of the bromide Compound 1.1 (63.0 mmol theoretical) in dry diethyl ether (500 ml) by canulation. The reaction mixture was stirred at room temperature under argon-atmosphere for 72 hours. Subsequently the reaction mixture was poured out into water (2000 ml), and acetic acid (200 ml) was added to dissolve the magnesium-salts. The two layers were separated, and the organic layer was washed with water (3×500 ml). The combined aqueous layers were concentrated under reduced pressure to yield a light brown solid residue. This residue was dissolved in pyridine (500 ml). At 0° C. acetic anhydride (340 ml) was added slowly. After adding DMAP (200 mg, 1.64 mmol), stirring was continued for 20 hours at room temperature under argon-atmosphere. Next the reaction mixture was concentrated under reduced pressure, followed by azeotropic distillation with toluene (1×250 ml), and the addition of diethyl ether (3 1). The obtained organic layer was washed with sat. NaHCO$_3$-sol. (2×1l), 1 N HCl-sol. (2×1l) and water (2×1l). Drying on MgSO$_4$, and concentrating under reduced pressure, yielded 25.1 g light brown crystals. These were purified by recrystallization from 2-propanol, to give 16.1 g Compound 2.2 (63%) as white crystals.

Formula: $C_{20}H_{24}O_9$ Molecular weight: 408.40 R$_f$: 0.42 (cyclohexane/ethyl acetate 1:1) Melting point: 149–150° C. IR (KBr): 2956, 1753, 1433, 1368, 1224, 1104, 1036, 978, 916, 764, 738, 702, 603 cm$^{-1}$ ES-MS: 431=[408+Na]$^{+1}$H-NMR (500 MHz, CDCl$_3$): [δ (ppm); J (Hz)] 7.39 (5H, m), 5.24 (1H, dd, app. t, J=9.4), 5.24 (1H, dd, app. t, J=9.8), 5.14 (1H, dd, app. t, J=9.8), 4.40 (1H, d, J=9.9), 4.30 (1H, dd, J=17.2, 4.7), 4.16 (1H, dd, J=12.2, 1.5), 3.85 (1H, m), 2.09 (3H, s), 2.06 (3H, s), 2.01 (3H, s), 1.80 (3H, s) $^{13}$C-NMR (125 MHz, CDCl$_3$): δ (ppm) 170.60, 170.25, 169.36, 168.70, 136.01, 128.75, 128.28, 126.96, 80.08, 75.94, 74.06, 72.44, 68.39, 62.17, 20.61, 20.48, 20.21

Synthesis of Compound 1.3

To a solution of the tetra-acetate, Compound 2.2, (16.08 g, 39.4 mmol) in a mixture of tetrahydrofuran (232 ml) and methanol (232 ml) was added anhydric potassium carbonate (1.36 g, 9.84 mmol, 0.25 eq). The mixture was stirred at room temperature under argon-atmosphere for 3 hours. Silicagel (40 ml) was added and the solvent was removed under reduced pressure. Purification of the product Compound 1.3 by column chromatography (dichloromethane/methanol 85/15) gives 9.50 g of product Compound 2.3 (99%).

Formula: $C_{12}H_{16}O_5$ Molecular weight: 240.26 R$_f$: 0.12 (dichloromethane/methanol 9:1) IR (KBr): 3368, 2919, 2360, 1636, 1496, 1455, 1082, 1042, 891, 764, 701, 595 cm$^{-1}$ ES-MS: 258=[240+NH$_4$]$^+$, 263=[240+Na]$^{+1}$H-NMR (500 MHz, CDCl$_3$): [(ppm); J (Hz)] 7.44 (2H, d, J=7.1), 7.35 (2H, dd, app. t, j=7.6), 7.30 (1H, m), 4.15 (1H, d, J=9.4), 3.90 (1H, dd, J=12.1, 1.6), 3.72 (1H, dd, J=12.0, 5.2), 3.51 (1H, dd, app. t, J=8.7), 3.45 (1H, dd, app. t, J=9.4), 3.43 (3H, m), 3.40 (1H, dd, app. t, J=9.2) $^{13}$C-NMR (125 MHz, CDCl$_3$): δ (ppm) 139.30, 127.43, 82.41, 80.70, 78.23, 74.98, 70.40, 61.41

Synthesis of Compound 2.4

To a solution of tetrol Compound 2.3 (1.15 g, 4.79 mmol) in dry acetonitrile (3 ml) under argon-atmosphere was added camphorsulfonic acid (279 mg, 1.20 mmol, 0.25 eq) and benzaldehyde dimethyl acetal (1.44 ml, 9.58 mmol, 2 eq). The reaction mixture was stirred at room temperature for 3 hours. Subsequently the mixture was neutralized by addition of triethylamine (0.337 ml, 2.40 mmol). Concentrating the reaction mixture under reduced pressure yields 2.70 g of a light yellow oil. Purification by column chromatography (CH$_2$Cl$_2$/iPrOH 1/1) gives 1.53 g of Compound 2.4 (97%) as a white solid.

Formula: $C_{19}H_{20}O_5$ Molecular weight: 328.36 R$_f$: 0.27 (cyclohexane/ethyl acetate 1:1) Melting point: 114–115° C. [α]$_D^{20}$=+9.30°; [α]$_{365}^{20}$=+10.0°(c=1.13 in chloroform) IR (KBr): 3433, 2874, 2357, 1651, 1496, 1455, 1385, 1313, 1272, 1211, 1109, 1029, 1009, 913, 765, 733, 700 cm$^{-1}$ ES-MS: 346=[328+NH4]$^{+1}$H-NMR (500 MHz, CDCl$_3$): [δ (ppm); J (Hz)] 7.53 (2H, m), 7.40 (5H, m), 7.39 (3H, m), 5.59 (1H, s), 4.37 (1H, dd, J=10.3, 5.9), 4.30 (1H, d, J=9.3), 3.91 (1H, dd, app. t, J=8.6), 3.79 (1H, dd, app. t, J=10.3), 3.67 (1H, dd, app. t, J=9.3), 3.65 (1H, m), 3.63 (1H, m) $^{13}$C-NMR (125 MHz, CDCl$_3$): (ppm) 137.50, 136.84, 129.14, 128.65, 128.52, 128.20, 127.29, 126.12, 101.73, 82.41, 80.90, 75.43, 74.60, 70.60, 68.70

Synthesis of Compound 2.5

To an ice-cooled solution of the diol, Compound 2.4 (500 mg; 1.523 mmol), in dry pyridine (15 ml) successively DMAP (20 mg; 0.15 mmol; 0.1 eq.) and Ac$_2$O (5 ml) are added. The cooling is removed and the reaction mixture is stirred for 18 hours under Ar atmosphere at room temperature. Then pyridine and Ac$_2$O are removed azeotropically under reduced pressure using toluene. The residue is purified by column chromatography (Merck kieselgel; cyclohexaan/EtOAc: 85/15). Compound 2.5 is obtained in 95% yield (595 mg; 1.443 mmol).

Formula: $C_{23}H_{24}O_5$ Molecular weight: 412.4 R$_f$: 0.21 (cyclohexane/EtOAc: 85/15) Melting point: >150° C. sublimation [α]D$^{20}$:−78.46° (c=1.010; CHCl$_3$) IR (KBr-disc, film): (cm$^{-1}$) 3065 (w); 3033 (w); 2948 (w); 2873 (w); 2863 (w); 1749 (s); 1370 (m); 1238 (s); 1212 (s); 1105 (s); 1063 (m); 1031 (m); 999 (m); 767 (m); 701 (m)

MS (m/z): 43 (100); 91 (17); 105 (26); 107 (13); 189 (9); 219 (11); 352 (3); 369 (<1) $^1$H-NMR (500 MHz; CD$_3$COCD$_3$): [δ (ppm); J (Hz)] 7.46 (2H; m); 7.39 (2H; m); 7.34 (6H; m); 5.69 (1H; s); 5.42 (1H; dd(app.t); J=9.5); 5.19 (1H; dd(app.t); J=9.5); 4.67 (1H; d; J=9.8); 4.31 (1H; dd; J=4.6, 9.9); 4.98 (1H; dd(app.t); J=9.4); 3.87 (1H; dd(app.t); J=10.0); 3.82 (1H; ddd; J=4.6, 9.5, 10.0); 1.95 (3H; s); 1.76 (3H; s) APT (125 MHz; CD$_3$COCD$_3$): δ (ppm) 20.3 (CH$_3$); 20.7 (CH$_3$); 69.1 (CH$_2$); 71.7 (CH); 73.8 (CH); 74.3 (CH); 79.6 (CH); 81.2 (CH); 102.1 (CH); 127.2 (CH); 128.2 (CH);

128.8 (CH); 129.0 (CH); 129.3 (CH); 129.6 (CH); 138.3 (C); 138.7 (C); 169.2 (C); 170.3 (C)

Synthesis of Compound 2.6

Compound 2.5 (400 mg; 0.970 mmol) is dissolved in dry toluene (5 ml) and a 0.5M solution of the Petasis reagent ($Cp_2TiMe_2$) in toluene (8.15 ml; 4.074 mmol; 4.2 eq.) is added dropwise. The reaction mixture is covered from light and is heated at 70° C. for 60 hours under Ar atmosphere. The reaction mixture is then concentrated under reduced pressure and the residue is purified by column chromatography (Merck kieselgel; cyclohexane/$CH_2Cl_2$/EtOAc: 50/50/1).

Synthesis of Compound A3

To a solution of the enol ether 2.6 (320 mg; 0.783 mmol) in dry EtOAc (17 ml) is added dry $Et_3N$ (1.7 ml). Then Pd/C (10% wt palladium; 320 mg) is added and the reaction mixture was put under $H_2$ atmosphere. After stirring at room temperature for 22 hours the catalyst is removed by filtration over celite and is washed with EtOAc. The residue obtained after concentration of the filtrate is purified by column chromatography (Merck kieselgel; pentane/$CH_2Cl_2$/ether: 50/50/1). Compound A3 is obtained in 82% yield (265 mg; 0.642 mmol).

Formula $C_{25}H_{32}O_5$ Molecular weight: 0.22 (pentane$CH_2Cl_2$/ether: 50/50/1) Melting point: 98–100° C. $[\alpha]_D^{20}$: −31.02° (c=1.100; $CHCl_3$) IR (KBr-disc, film): ($cm^{-1}$) 3066 (w); 3035 (w); 2972 (s); 2925 (m); 2902 (m); 2869 (m); 1454 (m); 1380 (m); 1170 (m); 1106 (s); 1076 (s); 1028 (s); 1001 (m); 764 (m); 748 (m); 700 (s) MS (m/z): 43 (100); 91 (62); 105 (69); 107 (56); 115 (20); 149 (88); 196 (4); 238 (12); 263 (7); 369 (<1); 412 (<1; $M^{+\circ}$) $^1$H-NMR (500 MHz; $CD_3COCD_3$): [δ (ppm); J (Hz)] 7.51 (2H; m); 7.27–7.43 (8H; m); 5.65 (1H; s); 4.25 (1H; d; J=9.2); 4.23 (1H; dd; J=5.0, 10.2); 4.01 (1H; h; J=6.1); 3.76 (1H; dd(app.t); J=10.1); 3.66 (1H; dd(app.t); J=9.2); 3.62 (1H; dd(app.t); J=9.2); 3.55 (1H; ddd; J=5.0, 9.1, 9.9); 3.28 (1H; dd; J=8.3, 9.2); 3.19 (1H; h; J=6.1); 1.14 (6H; 2d(app.t); J=5.9); 0.96 (3H; d; J=6.1); 0.44 (3H; d; J=6.1) APT (125 MHz; $CD_3COCD_3$): δ (ppm) 21.9 ($CH_3$); 22.7 ($CH_3$); 23.0 ($CH_3$); 23.6 ($CH_3$); 69.4 ($CH_2$); 71.6 (CH); 72.8 (CH); 73.3 (CH); 80.9 (CH); 81.5 (CH); 83.1 (CH); 83.8 (CH); 101.7 (CH); 126.9 (CH); 128.6 (CH); 128.8 (CH); 128.8 (CH); 129.4 (CH); 139.3 (C); 140.7 (C)

Screening of the Compounds for Bioactivity

The compounds were screened against various pathogenic viruses such as the human immunodeficiency virus (HIV), herpes simplex virus (HSV), vaccinia virus (VV), the varicella zoster virus (VZV) and the human cytomegalo virus (CMV). For all viruses, except for CMV, the $EC_{50}$ (effective compound concentration required to inhibit HIV-induced cytopathicity in human CEM cell cultures, HSV- and VV-induced cytopathicity in human embryo fibroblast $E_6SM$ cell cultures, and VZV-induced plaque formation in human embryonic lung HEL cell cultures by 50%.) was determined. For determination of the antiviral activity, expressed in $IC_{50}$, against CMV, human embryonic lung fibroblast (HEL) cells grown in 96-well microplates were infected with 20 PFU virus/well.

After 2 hours of incubation at 37° C., the infected cells were replenished with 0.1 ml of medium containing serial dilutions of the test compound. On day 7 the plaques were counted microscopically after staining the cells with Giemsa's solution. The minimum antiviral concentration was expressed as the dose required to inhibit virus-induced plaque formation by 50%.

The compounds were also screened against flaviviruses. Due to the fact that there is no adequate in vitro assay to screen against HCV, we opted to screen against the bovine viral diarrhea virus (BVDV), as it shares many similarities with the hepatitis C virus. Antiviral activity was assessed using the Pe 515 strain of BVDV on Madin Darby bovine kidney cells (MDBK cells). Both antiviral activity and cytotoxicity was determined by means of the MTS method. The $EC_{50}$ is the concentration required to reduce virus induced cytopathic effect by 50%. The MTC (minimal toxic concentration) was defined as the concentration that caused >=20% reduction in cell metabolism.

The compounds were also checked for anti-tumor activity via the proliferation of murine leukemia cells (L 1210/0), murine mammary carcinoma cells (FM3A) and human T-lymphocyte cells (Molt4/C8, CEM/0).

Based on the NCCLS documents M7-A4, Vol. 17 No. 2, M27-A, Vol 17 No. 9 and M38-P, Vol 18 No. 13, a microdilution method for conducting the antibacterial and antifungal screenings was developed using a Bioscreen C Analyser (Labsystems, Finland), which is an automated reader-incubator. It measures growth continuously by vertical photometry (optical density), processes the data and provides a print-out of the results. For the bacteria we selected as primary target: *Staphylococcus aureus* ATCC29213, *Enterococcus faecalis*ATCC 29212, *Escherichia coli* ATCC 25922 and *Pseudomonas aeruginosa* ATCC 27853. *Candida albicans* ATCC 24433 and *Cryptococcus neoformans* ATCC 90112 were selected as yeast targets. The dermatophyte *Trichophyton mentagrophytes* ATCC 9533 and the invasive mould *Aspergillus fumigatus* ATCC 2895 were selected as moulds. All parameters necessary for optimal incubation can be programmed in the Biolink-software (Labsystems, Finland). Incubation for all bacterial screenings was 16 hours at 35° C. The incubation parameters for the screenings against *Candida* and *Cryptococcus* were respectively 24 and 48 hours at 35° C., the invasive fungus *Aspergillus fumigatus* was incubated for 3 days at 30° C. and the dermatophyte *T. mentagrophytes* was incubated for 5 days at 30° C. As growth media for the bacteria cation adjusted Mueller-Hinton broth (Oxoid, Belgium) was used. A synthetic medium is recommended for fungal susceptibility tests: RPMI 1640, with glutamine, and without bicarbonate and with a pH indicator (Oxoid), supplemented with 1% glucose.25 μl of a 10-fold compound concentration is pipetted into each well. To each 25 μl test compound 225 μl of growth media was added. As measurement tool for the antibacterial and anti-yeast screenings, the area under the growth curve is used, which is automatically determined via the Biolink software. For the screenings against the pathogenic moulds we used endpoint OD-measurement. For internal quality control, reference antibiotics for each micro-organism are incorporated in the set-up of the tests.

Results and Discussion

In a first set of screenings (Table 1), the anti-viral activity of the bicyclic carbohydrates was checked against HIV-1, HIV-2, HSV-1, HSV-2, VV, CMV and VZV. Only compound A3 showed activity against VZV.

TABLE 1

Results of screenings against HIV-1, HIV-2,
HSV-1, HSV-2, VV, CMV and VZV

| | $^a$EC$_{50}$ (µg/ml) | | | | | | | |
|---|---|---|---|---|---|---|---|---|
| Compound | HIV-1 (III$_B$) (CEM) | HIV-2 (ROD) (CEM) | HSV-1 (KOS) (E$_6$SM) | HSV-2 (G) (E$_6$SM) | VV (E$_6$SM) | CMV Davis, AD-169 (HEL) | VZV (HEL) OKA | VZV (HEL) YS |
| Compound A1 | >20 | >4 | >16 | >16 | >16 | >20 | ND | ND |
| Compound A2 | >20 | >20 | >16 | >16 | >16 | >20 | ND | ND |
| Compound A3 | >20 | >4 | >8 | >8 | ND | >5 | 1.1 | ND |

$^a$50% Effective concentration or compound concentration required to inhibit HIV-induced cytopathicity in human lymphocyte CEM cell cultures, HSV- and VV-induced cytopathicity in human embryo fibroblast E$_6$SM cell cultures, and CMV- and VZV-induced plaque formation in human embryonic lung HEL cell cultures by 50%.

TABLE 2

Results of screenings against BVDV in MDBK cells

| Compound | EC$_{50}$ (µg/ml) BVDV | MTC (µg/ml) MDBK |
|---|---|---|
| Compound A1 | 23/4/3.2 | >100/>100/>100 |
| Compound A2 | 7/53/54 | >100/>100/>100 |
| Compound A3 | <0.8 | >100 |
| Ribavirin | 40 | — |

A second series of viral screenings (Table 2) was performed in order to check anti-bovine viral diarrhea virus (BVDV—strain Pe515) activity in bovine kidney (MDBK) cells. Compound A1 had an EC$_{50}$ of respectively 23, 4, and 3.2 µg/ml. Compound A2 had an EC$_{50}$ of respectively 7, 53, and 54 µg/ml. Replication test with both compounds were all three independent experiments. Compound A3 had an EC$_{50}$<0.8 µg/ml. Ribavirin is the golden standard that currently is used to treat infections caused by HCV. From the results in Table 2 it is clear that Compounds A1, A2 and A3 are much more active than Ribavirin.

The MTC was not reached at the highest concentration (100 µg/ml) for MDBK cells when treated with Compounds A1, A2 and A3.

The anti-tumor activity of Compound A1 was screened against L1210/0, FM3A/0, Molt4/C8 and CEM/0. No antitumor activity was noticed for Compound A1 against all tested cell-lines. Compound A2 showed moderate antitumor activity against the tested cell-lines (Table 3).

TABLE 3

Results of the anti-tumor screenings against
L1210/0, FM3A/0, Molt4/C8 and CEM/0

| | IC$_{50}$ (µg/ml) | | | |
|---|---|---|---|---|
| Compound | L1210/0 | FM3A/0 | Molt4/C8 | CEM/0 |
| Compound A1 | >200 | >200 | >200 | >200 |
| Compound A2 | 82 ± 7 | 22 ± 0 | 19 ± 1 | 27 ± 2 |
| Compound A3 | N.A. | N.A. | N.A. | N.A. |

The antibacterial activity was screened against four reference bacteria; *S. aureus*, *E. faecalis*, *E. coli* and *P. aeruginosa* (Table 4). None of the compounds showed any significant antibacterial effect against the selected micro-organisms. The minimum inhibition concentration for both compounds was above 25 µg/ml.

TABLE 4

Results of the antibacterial screenings against
Gram positive and Gram negative species

| | MIC (µg/ml) | | | |
|---|---|---|---|---|
| Compound | S. aureus ATCC 29213 | E. faecalis ATCC 29212 | E. coli ATCC 25922 | P. aeruginosa ATCC 27853 |
| Compound A1 | >25 | >25 | >25 | >25 |
| Compound A2 | >25 | >25 | >25 | >25 |
| Compound A3 | >25 | >25 | >25 | >25 |

The antifungal activity was screened against two pathogenic yeasts and molds (Table 5). None of the compounds showed any significant antifungal effect against the selected micro-organisms. The minimum inhibition concentration for both compounds was above 25 µg/ml.

TABLE 5

Results of the screenings against pathogenic fungi

| | MIC (µg/ml) | | | |
|---|---|---|---|---|
| Compound | C. albicans ATCC 24433 | C. neoformans ATCC 90112 | T. mentagrophytes ATCC 9533 | A. fumigatus ATCC 2895 |
| Compound A1 | >25 | >25 | >25 | >25 |
| Compound A2 | >25 | >25 | >25 | >25 |
| Compound A3 | >25 | >25 | >25 | >25 |

CONCLUSION

In the first set of screenings against DNA- and retroviruses no significant antiviral activity was observed. However, in the second set of screenings against BVDV (RNA virus) we clearly found significant anti-viral activity of Compound A1 and Compound A3 and moderate activity for Compound A2. Other bicyclic carbohydrates tested up to now showed no activity against BVDV. Furthermore, no significant anti-tumor, or antimicrobial activity was observed. Since BVDV and HCV share many similarities, Compound A1 and Compound A3 and probably other bicyclic carbohydrates, may have strong and selective antiviral properties against HCV. In addition the Compound A1, Compound A2 and Compound A3 could also show activity against other *Flaviviridae* such as West Nile virus and Dengue virus. From the screenings it is clear that Compounds A1, A2 and A3 exhibit a stronger antiviral activity against *Flaviviridae* compared to Ribavirin, which is the current golden standard that is used to treat infections caused by e.g. HCV.

Although the invention has been described with respect to a preferred embodiment thereof, it is to be also understood that it is not to be so limited since changes and modifications can be made therein which are within the full intended scope of this invention as defined by the appended claims.

What is claimed is:

1. A method of treating infections caused by *Flaviviridae* sp., comprising the step of administering an effective amount of a bicyclic carbohydrate having the formula:

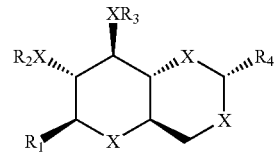

wherein:
$R_1$ is selected from the group consisting of -alkyl, -aryl and -benzyl;
$R_2$ and $R_3$ are selected from the group consisting of -alkyl and -aryl;
$R_4$ is an -aryl; and
X is O;
or a pharmaceutically active salt thereof.

2. A method as defined in claim 1, wherein $R_1$ is selected from the group consisting of phenyl and benzyl, $R_2$ and $R_3$ are selected from the group consisting of propyl, i-propyl and butyl, $R_4$ is phenyl.

3. A method as defined in claim 1, wherein the infection is hepatitis C.

4. A method as defined in claim 1, wherein the infection is bovine viral diarrhea.

5. A method of treating infections caused by (+) sense RNA viruses, comprising the step of administering an effective amount of a compound of claim 1.

* * * * *